United States Patent
Wang et al.

(10) Patent No.: US 8,000,806 B2
(45) Date of Patent: Aug. 16, 2011

(54) NEURAL CHANNEL BRIDGE AIDED BY A MICRO-ELECTRONIC SYSTEM

(75) Inventors: Zhigong Wang, Jiangsu (CN); Xiaosong Gu, Jiangsu (CN); Xiaoying Lv, Jiangsu (CN)

(73) Assignees: Southeast University, Nanjing, Jiangsu (CN); Nantong University, Nantong, Jiangsu (CN)

( * ) Notice: Subject to any disclaimer, the term of this patent is extended or adjusted under 35 U.S.C. 154(b) by 281 days.

(21) Appl. No.: 12/159,776

(22) PCT Filed: Dec. 25, 2006

(86) PCT No.: PCT/CN2006/003580
§ 371 (c)(1),
(2), (4) Date: Oct. 9, 2008

(87) PCT Pub. No.: WO2007/076690
PCT Pub. Date: Jul. 12, 2007

(65) Prior Publication Data
US 2009/0112286 A1    Apr. 30, 2009

(30) Foreign Application Priority Data
Dec. 30, 2005 (CN) .......................... 2005 1 0135541

(51) Int. Cl.
*A61N 1/00* (2006.01)
(52) U.S. Cl. ........................ 607/118; 607/2
(58) Field of Classification Search .................. None
See application file for complete search history.

(56) References Cited

U.S. PATENT DOCUMENTS

| 4,308,868 | A | | 1/1982 | Jhabvala | |
|---|---|---|---|---|---|
| 4,878,913 | A | * | 11/1989 | Aebischer et al. | 623/23.64 |
| 5,030,225 | A | * | 7/1991 | Aebischer et al. | 606/152 |
| 5,048,522 | A | * | 9/1991 | Petrofsky | 607/69 |
| 5,314,457 | A | | 5/1994 | Jeutter et al. | |
| 5,358,514 | A | | 10/1994 | Schulman et al. | |
| 5,938,593 | A | * | 8/1999 | Ouellette | 600/300 |
| 2005/0251221 | A1 | * | 11/2005 | Zdravkovic | 607/46 |
| 2006/0015028 | A1 | * | 1/2006 | Finneran et al. | 600/393 |
| 2006/0282127 | A1 | * | 12/2006 | Zealear | 607/42 |

FOREIGN PATENT DOCUMENTS
WO    WO2005113062    12/2005

* cited by examiner

*Primary Examiner* — Niketa Patel
*Assistant Examiner* — Catherine Voorhees
(74) *Attorney, Agent, or Firm* — Knobbe, Martens, Olson & Bear, LLP

(57) ABSTRACT

Methods and equipment used to regenerate sensory, motorial, or visceral signals of injured, broken or diseased nerves of mammalia, such as humans, are provided. In some embodiments, a lineup of downward and upward channels to bridge injured neural channels is disclosed. The downward or upward channels can be connected to electrodes which are in contact with upper or lower nerve stumps. The channels can be used to detect, amplify, and recognize the motorial or sensory signals, to generate related Functional Electrical Stimulation (FES) signals, and to supply the FES signals to the electrodes on the lower or upper nerve stumps. Neural signals can thus be regenerated and the injured motorial or sensory channels can be bridged.

9 Claims, 2 Drawing Sheets

US 8,000,806 B2

NEURAL CHANNEL BRIDGE AIDED BY A MICRO-ELECTRONIC SYSTEM

CROSS-REFERENCE TO RELATED APPLICATIONS

This application is a national stage application under 35 U.S.C. §371 of PCT Application No. PCT/CN2006/003580 designating the United States, filed Dec. 25, 2006. The PCT Application was published in English as WO 2007/076690 A1 on Jul. 12, 2007 and claims the benefit of the earlier filing date of Chinese Patent Application No. 200510135541.6, filed Dec. 30, 2005. The contents of Chinese Patent Application No. 200510135541.6 and International Application No. PCT/CN2006/003580 including the publication WO 2007/076690 A1 are incorporated herein by reference in their entirety.

TECHNICAL FIELD

The present inventions relate to methods for regeneration as well as related equipment.

BACKGROUND

The regeneration of injured nerves is a significant subject in neurobiology. Nerve regeneration may activate the neurons at the injured points to grow through some guidance channels to connect the upper and lower nerve channels again. Recently, Anderson's group (UC Irvine, USA) has used adult human neural stem cells to regenerate injured spinal cord tissue and improve the mobility in mice. (PNAS, Sep. 27, 2005). However, there are still some problems left.

In their experiments, they injected human stem cells into the spinal cord of a mouse after it had been injured for 9 days. The problem with this approach is determining the valid waiting period to inject stem cells into a human body, because it is unknown how long 9 days for mice may be for a human. For example, it took 4 months for the mice to crawl. How many days does this equal for a human?

During the feeding, the mice's immune system was controlled. This may present some serious problems when the same method is applied to the human body.

Other experiments showed that, this method may be invalid to those spinal cords which have been injured for longer than 6 months. These factors show that even with the help of human neural stem cells there is still a long way to realize the functional regeneration of injured human spinal cords. Accordingly, it may be advantageous to provide additional methods to lead signals from a nerve fiber from one end to the other.

SUMMARY

In some embodiments, a method and related equipment which uses a microelectronic system to bridge injured nerves is provided. For example, a method used for the regeneration of the sensory, motorial, or visceral signals of injured nerves, including broken or diseased nerves of mammalia (e.g. humans), as well as related equipment is provided. The method and equipment may use a microelectronic system.

In exemplary embodiments, regeneration of the sensory, motor or viscus signals of injured nerves of mammalia, including a human is provided. This may include a lineup of downward and upward channels that include a microelectronic system to bridge the injured neural channels. In an embodiment, the downward channels are connected to the electrodes which are in contact with the upper nerve stump (on top of the injured section), to detect, amplify, and/or recognize the motorial signals, to generate the Functional Electrical Stimulation (FES) signals, and to supply the FES signals to the electrodes on the lower nerve stump (below the injured section), so that neural signals can be regenerated and the injured motorial channels can be bridged. The upward channels may be connected to the detecting electrodes on the lower nerve stump, and after the sensory neural signals are detected and processed, related FES signals are generated to stimulate the upper electrodes, so that the injured sensory channels can be bridged.

The equipment described may include a downward channel and/or an upward channel. The downward channel may include an array of detecting electrodes, an amplifier, a signal processor, a stimulator, and an array of stimulating electrodes. The detecting electrodes are used to detect the motorial signals from the upper nerve stump. The amplifier amplifies the signal to desired amplitude. The signal processor is used to recognize the neural signal. The stimulator is used to generate a FES signal and to drive the stimulating electrodes on the lower nerve stump, so that the interrupted motorial signals can be regenerated in the lower nerve.

The upward channel can include an array of detecting electrodes, an amplifier, a signal processor, a stimulator, and an array of stimulating electrodes. However, the detecting electrodes may be used to detect the sensory signals from the lower nerve stump. The amplifier amplifies the signal to the desired amplitude. The signal processor is used to recognize the neural signal. The stimulator is used to generate a FES signal and to drive the stimulating electrodes on the upper nerve stump, so that the interrupted sensory signals can be regenerated in the upper nerve.

The present disclosure may provide the following advantages. One or more weak neural signals can be obtained by the detecting electrodes from the upper or lower nerve stump, the weak signals are then processed by amplifying and recognizing before the desired FES signals are generated, and at last, the FES signals are utilized to stimulate the lower or upper nerve stumps. Thus, signal channels across injured nerves are bridged by the help of a micro-electronic system. The equipment may detect the signals from one end of the nerve stumps, process the signals, and stimulate the other end of the nerve stumps. In such a manner same neural signals are regenerated with the help of micro-electronic system. This disclosure realizes the nerve functional regeneration through a micro-electronic bridge which is connected onto two nerve stumps over the injured periphery nerve or spinal cord. With help of this equipment, for example, the neural function of some paraplegics caused by injured spinal cord can be partially recovered.

BRIEF DESCRIPTION OF THE FIGURES

The above-mentioned and other features of the inventions disclosed herein are described below with reference to the drawings of preferred embodiments. The illustrated embodiments are intended to illustrate, but not to limit the inventions. The drawings contain the following Figures.

DESCRIPTION OF THE EMBODIMENTS

Figure 1:
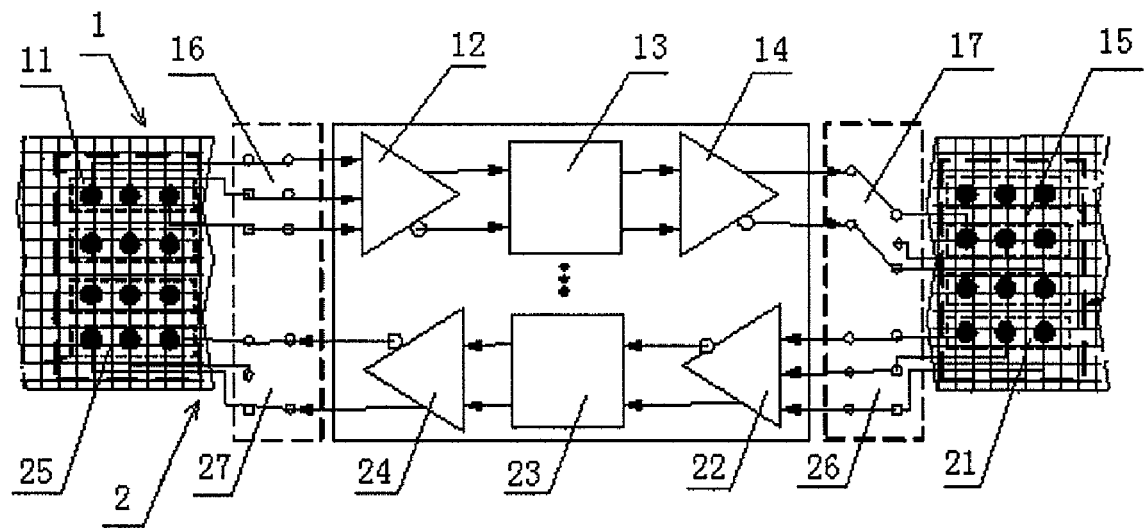
FIG. 1 is a functional diagram of a micro-electronic neural signal regeneration system of some embodiments.
Figure 2:
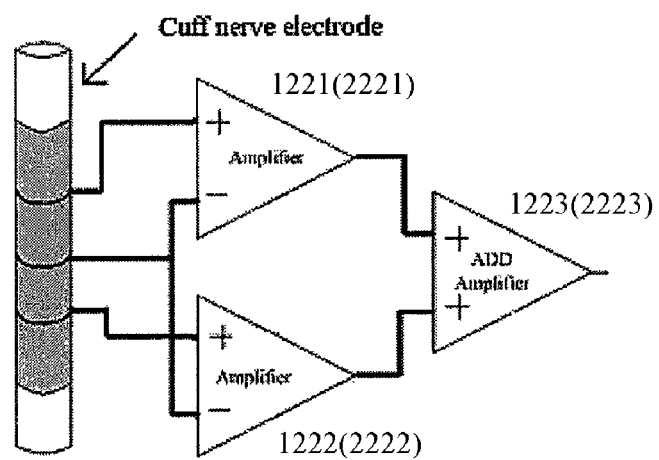
FIG. 2 is a diagram of an electrodes system of some embodiments.
Figure 3:
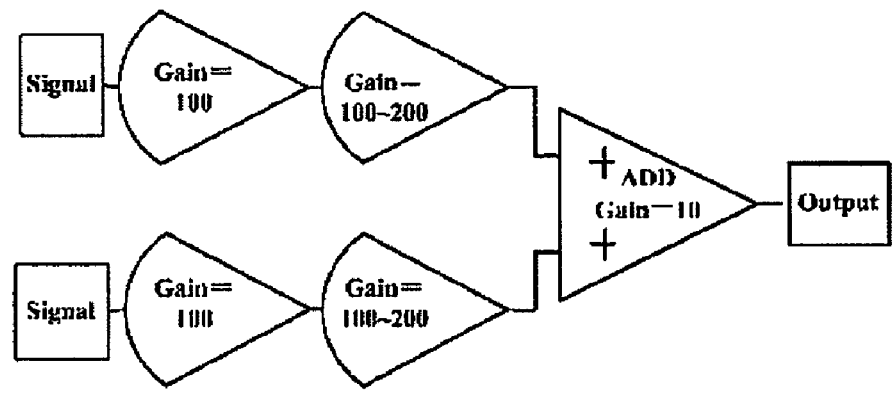
FIG. 3 is a diagram of amplifier circuits.
Figure 4:
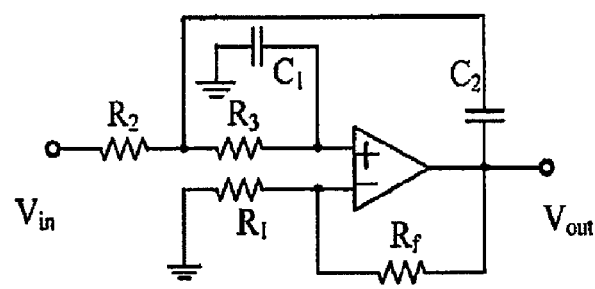
FIG. 4 is a diagram of a filter of some embodiments.

Embodiments used to regenerate the sensory, motor or viscus signals of injured nerves of Mammalia including human are provided, which have the feature of allowing a lineup of downward and upward channels that include a microelectronic system to bridge injured neural channels. In one embodiment, the downward channels can be connected to the electrodes which are contacted onto the upper nerve stump (on top of the injured section), to detect, to amplify, and to recognize the motorial signals, to generate the Functional Electrical Stimulation (FES) signals, and to supply the FES signals to the electrodes on the lower nerve stump (below the injured section), so that neural signals can be regenerated and the injured motorial channels can be bridged. In an embodiment, the upward channels may be connected to the detecting electrodes on the lower nerve stump, and after the sensory neural signals are detected and processed, related FES signals are generated to stimulate the upper electrodes, so that the injured sensory channels can be bridged.

For example, the motorial signals can be detected by the detecting electrodes, routed by the upper Switching Array (SA), amplified, filtered, and applied to the FES signal generators. The FES signals can then be routed by the lower SA to the stimulating electrodes.

In addition, the sensory signals can be detected by the detecting electrodes, routed by the lower SA, amplified, filtered, and applied to the FES signal generators. The FES signals can then be routed by the upper SA to the stimulating electrodes of upper sensory nerves. The upper and lower SAs may be used correlatively to make a correct switch among the upper and lower neural channels.

Equipment may be used that includes at least one downward microelectronic channel (1) and one upward microelectronic channel (2). In an embodiment, several ways of microelectronic channels can be used in parallel in both downward and upward directions. For example, we can choose a 2-way, 4-way or 8-way realization.

The downward microelectronic channel (1) mentioned above may include motorial signal detecting electrodes (11), amplifier (12), signal processor (13), stimulator (14), and stimulating electrodes (15). The motorial signals of upper nerve stump are detected by the detecting electrodes (11), amplified by the amplifier (12), processed by the processor (13), and supplied to the motorial signal stimulator (14), where the FES signals are generated and applied to the motorial signal stimulating electrodes (15), so that the desired motorial signals are regenerated in the lower nerve stump.

The upward microelectronic channel (2) mentioned above may include sensory signal detecting electrodes (21), amplifier (22), signal processor (23), stimulator (24), and sensory signal stimulating electrodes (25). The sensory signals of lower nerve stump can be detected by the detecting electrodes (21), amplified by the amplifier (22), processed by the processor (23), and supplied to sensory signal stimulator (24), where the FES signals are generated and applied to the sensory signal stimulating electrodes (25), so that the desired sensory signals are regenerated in the upper nerve stump.

The contacting electrodes array on upper nerve stump can be adopted by both the motorial signal detecting electrodes (11) and the sensory signal stimulating electrodes (25). The first SA (16 and 27) can be inserted at the place between the contacting electrodes array and the motorial signal amplifier (12) as well as the sensory signal stimulator (24). The first SA (16 and 27) is used to correctly connect the motorial signal detecting electrodes (11) to amplifier (12) and the stimulator (24) to motorial signal stimulating electrodes (25).

The contacting electrodes array on lower nerve stump can be adopted by both the motorial signal stimulating electrodes (15) and the sensory signal detecting electrodes (21). The second SA (17 and 26) can be inserted at the place between the contacting electrodes array on lower nerve stump and the motorial signal stimulator (14) as well as the sensory signal amplifier (22). This second SA (17 and 26) is used to correctly connect the stimulator (14) to the motorial signal stimulating electrodes (15) and sensory signal detecting electrodes (21) to amplifier (22).

The signal processor (13 and 23) mentioned above is to recognize the nerve signals and may include an active low pass filter which is made of an RC network and an operational amplifier. Through the amplifier, the amplified signals are transmitted through the second and third resistor ($R_2$, $R_3$) and applied to the in-phase terminal of the operational amplifier (31). The first capacitance ($C_1$) is connected across the same in-phase terminal and the ground. There is a shunt (and the second) capacitance ($C_2$) between the common nodes of $R_2$ and $R_3$ and the output of the operational amplifier (31). The first resistor ($R_1$) is connected across the anti-phase terminal of the operational amplifier (31) and the ground. The shunt resistor Rf is connected across the anti-phase terminal and the output of the operational amplifier (31).

Both the downward neural signal amplifier (12) and the upward neural signal amplifier (22) mentioned above can include the first, the second amplifier (1221, 1222 or 2221, 2222) and the summing circuit (1223 or 2223). The output terminals of the first and the second amplifier (1221, 1222 or 2221, 2222) are connected to the input terminals of the summing circuit (1223 or 2223). The output terminals of the summing circuit (1223 or 2223) are considered as the output terminals of the downward neural signal amplifier (12) or the upward neural signal amplifier (22). The detecting electrodes (11 or 21) use cuff electrodes. Among the 3 contacts (not shown) in the same longitudinal line, the middle one is connected to the anti-phase terminals of the amplifiers mentioned above, 1221, 1222 or 2221, 2222, while the other two are connected to the in-phase terminals, respectively. The function of the neural signal amplifier is to amplify the weak signals detected by the electrodes to a defined amplitude for the further processing.

In some embodiments, both the detecting electrodes and stimulating electrodes can include 3 contacting points, such as, in the same line. As detecting electrodes, the 3 points build up a so-called "tri-polar system". As stimulating electrodes, 2 of them can be taken, for example, the outer two, to build up a differential system. Along with other electrodes, the downward motorial detecting electrodes (11) and the sensory-signal stimulating electrodes 25 build up an electrodes array, in which each of the 3 contacting points in a row could be used for either detecting or stimulating of neural signals. This can be dependent on their connecting to motorial or sensory nerve fiber.

In some embodiments, neural signal amplifying may be used, such that each neural signal source is equivalent to a weak voltage source with a high resistance. The amplitude of the voltage detected from the electrodes can be in the order of microvolt. At the same time, the neural source with a high-resistance can have a high noise and interference level because of in-body activities. This can be solved by using a high sensitivity, low noise amplifier. An amplifier with a high sensitivity can be used because neural signals are of a low frequency (400~4000 Hz). For example, using a standard 0.6 µm CMOS process a high gain, low power operational amplifier can be designed. Under a supply of 1.8 V, the open-loop gain can be 70.6 dB, the gain-bandwidth-product 3.42 MHz and the power consumption less than 20 µW.

Additionally, neural signal processing techniques can be used, such as after neural signals have been detected by the electrodes. This may improve signal processing. In particular, for active neural signal regeneration, one or more analog-to-digital converters (ADC), digital signal processors (DSP), and digital-to-analog converters (DAC) can be inserted. In order to simplify the circuits and reduce the power consumption, the architecture of an analog amplifier plus a filter, that is, the traditional analog signal processing, can be used.

In some embodiments, the function of the FES circuits can be to generate large currents or high voltage FES signals. Taking account of the uncertainty of the input resistance of a one-port network that may include stimulating electrodes and nerve tissue, a constant-current type of FES circuit can be used.

What is claimed is:

1. A method using a micro-electronic system (MES) for the regeneration of the sensory, motorial, or visceral signals of injured, broken or diseased nerves of a mammal, the system comprising downward and upward channels configured to bridge injured motorial and sensory neural channels, the method comprising:
   contacting at least a first electrode array onto an upper portion of a nerve stump which includes at least a first motorial nerve for carrying motorial neural signals and at least a first sensory nerve for carrying sensory neural signals;
   contacting at least a second electrode array onto a lower portion of the nerve stump which includes at least a second motorial nerve for carrying motorial neural signals and at least a second sensory nerve for carrying sensory neural signals;
   connecting at least a downward channel to the first and second electrode arrays;
   using the downward channel to detect, to amplify, and to recognize motorial signals from the first motorial nerve;
   generating motorial Functional Electrical Stimulation (FES) signals related to the detected motorial signals;
   supplying the motorial FES signals to the second electrode array on the lower nerve stump, so that the detected motorial neural signals can be regenerated and an injured motorial neural channel can be bridged;
   connecting at least an upward channel to the first and second electrode arrays;
   detecting and processing sensory neural signals from the second sensory nerve;
   generating sensory FES signals related to the detected sensory neural signals; and
   supplying the sensory FES signals through the first electrode array to the first sensory nerve, so that an injured neural sensory channel can be bridged.

2. The method according to claim 1, wherein the first electrode array contacting the upper portion of the nerve stump comprises at least downward detecting electrodes, wherein the second electrode array contacting the lower portion of the nerve stump comprises at least downward stimulating electrodes, the method further comprising:
   processing the motorial neural signals detected by the downward detecting electrodes only after passing through a First Switching Array ($SA_1$);
   supplying the motorial FES signals from a FES generator to the stimulating electrodes on the lower nerve stump only after they pass through a Second Switching Array ($SA_2$); and
   routing the injured motorial channels with $SA_1$ and $SA_2$.

3. The method according to the description in claim 1, wherein the first electrode array contacting the upper portion of the nerve stump comprises at least upward stimulating electrodes, wherein the second electrode array contacting the lower portion of the nerve stump comprises at least upward detecting electrodes, the method further comprising:
   processing the sensory neural signals detected by the upward detecting electrodes only after they pass through a Third Switching Array ($SA_3$);
   applying FES signals from a FES generator to the stimulating electrodes only after they pass through a Fourth Switching Array ($SA_4$); and
   correctly routing the injured sensory channels with $SA_3$ and $SA_4$.

4. A micro-electric system for performing the method of claim 1, wherein the at least one downward channel comprises downward detecting electrodes of the first electrode array, a downward amplifier, a downward signal processor, a downward stimulator and downward stimulating electrodes of the second electrode array, wherein the step of using comprises using the downward detecting electrodes to detect the motorial signals from an upper injured nerve stump, amplifying the notorial signal with the downward amplifier to such an amplitude that the signal can easily be processed by the downward processor, generating the motorial FES signals with the downward stimulator, and using the downward stimulating electrodes to apply the motorial FES signals to the lower nerve stump; and
   wherein the upward channel comprises upward detecting electrodes of the second electrode array, an upward amplifier, an upward signal processor, an upward stimulator and upward stimulating electrodes of the first electrode array, wherein the step of generating sensory FES signals to stimulate the first electrode array comprises using the upward detecting electrodes to detect the sensory signals from a lower injured nerve stump, amplifying the sensory signals with the upward amplifier to such an amplitude that the signal can easily be processed by the upward processor, generating the sensory FES signals with the upward stimulator, and using the upward stimulating electrodes to apply the sensory FES signals to the upper nerve stump for regeneration of the sensory signal.

5. The system according to claim 4 wherein the first electrode array comprises the downward detecting electrodes, the upward stimulating electrodes, a $SA_1$, and a $SA_4$, wherein the $SA_1$ is inserted at a place between the downward detecting electrodes and the downward amplifier and connects the downward amplifier with the first motorial nerve of the upper nerve stump, wherein $SA_4$ is inserted at the place between the upward stimulator and the upward stimulating electrodes and connects the upward stimulator to the first sensory nerve of the upper nerve stump; and
   wherein the second electrode array comprises the upward detecting electrodes, the downward stimulating electrodes, a $SA_2$ and a $SA_3$, wherein the $SA_2$ is inserted at a place between the downward stimulator and the downward stimulating electrodes and connects the downward stimulator with the second motorial erve of the lower nerve stump, and wherein $SA_3$ is inserted at a place between the upward detecting electrodes and the upward amplifier and connects the upward amplifier with the second sensory nerve of the lower nerve stump.

6. The system according to claim 4, wherein the signal processor comprises an active low pass filter consisting of an RC network and an operational amplifier (OPA), wherein the circuit is configured such that, through the operational amplifier, the amplified neural signals pass though second and third resistors ($R_2$, $R_3$) and act on an in-phase input terminal of the operational amplifier, wherein one terminal of a first capacitor ($C_1$) is connected at the same in-phase input terminal of OPA and the other terminal of $C_1$ is grounded, wherein a second capacitor ($C_2$) is connected over the common node of $R_2$ and $R_3$ and the output terminal of OPA, wherein one terminal of the first resistor ($R_1$) is connected at the anti-phase input terminal of OPA and the other terminal of $R_1$ is grounded, and wherein a shunt resistor Rf is connected over the anti-phase terminal and the output terminal of OPA.

7. The system according to claim 5, wherein the signal processor comprises an active low pass filter consisting of an RC network and an operational amplifier (OPA), wherein the circuit is configured such that, through the operational amplifier, the amplified neural signals pass though second and third resistors ($R_2$, $R_3$) and act on an in-phase input terminal of the operational amplifier, wherein one terminal of a first capacitor ($C_1$) is connected at the same in-phase input terminal of OPA and the other terminal of $C_1$ is grounded, wherein a second capacitor ($C_2$) is connected over the common node of $R_2$ and $R_3$ and the output terminal of OPA, wherein one terminal of the first resistor ($R_1$) is connected at the anti-phase input terminal of OPA and the other terminal of $R_1$ is grounded, and wherein a shunt resistor Rf is connected over the anti-phase terminal and the output terminal of OPA.

8. The system according to claim 4, wherein between the motorial signal detecting electrodes and the motorial signal processor there is a motorial signal amplifier, the system being configured such that the detected signals from the motorial detecting electrodes are amplified by the motorial signal amplifier and sent to the motorial signal processor, wherein between the sensory detecting electrodes and the sensory processor there is a sensory signal amplifier, and wherein the detected signals from the sensory signal detecting electrodes are amplified by the sensory signal amplifier and sent to the sensory signal processor.

9. The system according to claim 4 wherein both the motorial signal amplifier and the sensory signal amplifier consist of a first amplifier, a second amplifier, and a summing circuit, the output terminals of the first amplifier, the second amplifier are connected to the input terminals of the summing circuit, the output terminals of the summing circuit defining output terminals of the motorial signal amplifier or the sensory signal amplifier, the detecting electrodes comprising cuff electrodes, and wherein three contacts of the cuff electrode include a middle contact and two outer electrodes, the middle contact being connected to anti-phase terminals of the first and second amplifiers, the outer two contacts being connected to in-phase terminals of the first and second amplifiers respectively.

* * * * *